(12) United States Patent
Chi et al.

(10) Patent No.: US 10,329,533 B2
(45) Date of Patent: Jun. 25, 2019

(54) REGENERATIVE CELL AND ADIPOSE-DERIVED STEM CELL PROCESSING SYSTEM AND METHOD

(71) Applicant: Synova Life Sciences, LLC, Sacramento, CA (US)

(72) Inventors: John Chi, Sacramento, CA (US); James Lee, Sacramento, CA (US)

(73) Assignee: Synova Life Sciences, Inc., Alhambra, CA (US)

( * ) Notice: Subject to any disclaimer, the term of this patent is extended or adjusted under 35 U.S.C. 154(b) by 750 days.

(21) Appl. No.: 14/626,634

(22) Filed: Feb. 19, 2015

(65) Prior Publication Data

US 2015/0231244 A1  Aug. 20, 2015

Related U.S. Application Data

(60) Provisional application No. 61/941,964, filed on Feb. 19, 2014, provisional application No. 62/039,844, filed on Aug. 20, 2014.

(51) Int. Cl.
| | |
|---|---|
| *G01N 1/00* | (2006.01) |
| *C12N 5/0775* | (2010.01) |
| *C12M 1/33* | (2006.01) |
| *A61M 1/00* | (2006.01) |

(52) U.S. Cl.
CPC ........... *C12N 5/0667* (2013.01); *C12M 45/02* (2013.01); *A61M 1/00* (2013.01); *A61M 2202/08* (2013.01); *C12N 2509/10* (2013.01)

(58) Field of Classification Search
CPC .................................................. C12N 5/0667
See application file for complete search history.

(56) References Cited

U.S. PATENT DOCUMENTS

| | | | | |
|---|---|---|---|---|
| 5,728,130 | A * | 3/1998 | Ishikawa | A61B 17/3476 604/22 |
| 7,018,354 | B2 * | 3/2006 | Tazi | A61B 17/320068 604/22 |
| 2006/0051865 | A1 | 3/2006 | Higgins et al. | |
| 2009/0304644 | A1 | 12/2009 | Hedrick et al. | |
| 2010/0152880 | A1 * | 6/2010 | Boyden | A61K 9/0019 700/117 |
| 2012/0164113 | A1 | 6/2012 | Victor | |

FOREIGN PATENT DOCUMENTS

| | | |
|---|---|---|
| KR | 10-2009-000784 A | 1/2009 |
| WO | 2014-000031 A1 | 1/2014 |

OTHER PUBLICATIONS

International Search Report corresponding to PCT/US2015/016688 dated Apr. 30, 2015.

* cited by examiner

*Primary Examiner* — Jyoti Nagpaul
(74) *Attorney, Agent, or Firm* — Faegre Baker Daniels LLP (57) ABSTRACT

An adipose-derived stem cell (ASC), regenerative cell and/or regenerative factor processing system including a tissue extraction device for extracting raw tissue, such as adipose tissue, from a patient, an ASC, regenerative cell and/or regenerative factor isolator, and an implantation device for re-introducing the isolated ASCs, regenerative cells and/or regenerative factors into the patient.

12 Claims, 6 Drawing Sheets

REGENERATIVE CELL AND ADIPOSE-DERIVED STEM CELL PROCESSING SYSTEM AND METHOD

CROSS-REFERENCE TO RELATED APPLICATIONS

This patent application is a non-provisional patent application of and claims priority to U.S. Patent Application Ser. No. 61/941,964 titled Non-Cavitating Targeted Ultrasonic Dissociation of Adipose Tissue to Derive Stromal Vascular Fraction or Mesenchymal Fractions and Regenerative Cells, and filed Feb. 19, 2014, and U.S. Patent Application Ser. No. 62/039,844 titled Non-Cavitating Targeted Ultrasonic Dissociation of Adipose Tissue to Derive Stromal Vascular Fraction or Mesenchymal Fractions and Regenerative Cells, and filed Aug. 20, 2014, which are incorporated by reference in their entireties.

BACKGROUND OF THE INVENTION

1. Technical Field

Aspects of the present disclosure relate to medical processing devices and, in particular, to an adipose-derived stem cell processing system and method.

2. Discussion of Related Art

Stem cells, such as adipose-derived stem cells (ASCs), may be harvested from various parts of the human body, such as adipose tissue. ASCs are easily harvested by liposuction and, in most patients, a large quantity of ASCs can be obtained without substantial harm to the donor. It has been shown that a human lipoaspirate contains pluripotent and multipotent cells and may represent an alternative stem cell source to bone marrow-derived mesenchymal stem cells and embryonic stem cells. ASCs are capable of proliferation in monolayer culture and multilineage differentiation in response to inductive conditions, and thus have potential clinical application.

Interest in the field of regenerative medicine has shown promise in treating conditions, such as Parkinson's disease, Alzheimer's disease and cancers. This is accomplished through the implantation of stem cells which can be found in both embryonic and adult tissues. While much of the focus on stem cell shortage has focused on the embryonic sources, harvesting of embryonic stem cells has resulted in a great deal of ethical and political debate. Therefore, many scientists have turned to adult sources of stem cells, including adipose tissue, brain tissue, bone marrow, peripheral blood, blood vessels, skeletal muscle, skin, teeth, heart, gut, liver, ovarian epithelium, and testes.

Adipose tissue has been identified as an endocrine organ, in addition to its originally identified purpose of energy storage. By secreting bioactive molecules, called adipokines, this tissue plays an active role in the regulation of several bodily functions. Cellular content of adipose tissue includes specialized cells such as adipocytes and a stromal vascular fraction containing pre-adipocytes (which can differentiate into adipocytes), fibroblastic cells, endothelial cells, macrophages, and lymphocytes.

An adult stem cell is thought to be an undifferentiated cell, found among differentiated cells in a tissue or organ, that can renew itself and can differentiate to yield some or all of the major specialized cell types of the tissue or organ. Typically, there are a very small number of stem cells in each tissue, and once removed from the body generation of large quantities of stem cells is difficult. A need therefore exists to find a safe and efficient means of harvesting these stem cells from live tissue.

Current methods of harvesting mesenchymal stem cells from adipose tissue have severe drawbacks which limit their efficacy and both result in significant destruction of the original tissue. Such methods face problems with enzyme source, consistency, concentration, potency and manufacture. In one such method, mesenchymal stem cells are removed from adipose tissue through the use of an enzymatic digestion step. The enzyme must be diluted and washed from the cell culture when digestion is complete, but trace levels can remain. These enzymes may also damage the integrity of the cell walls. Therefore, there is a need for a method which will not significantly harm the surrounding adipose tissue or extracellular matrix during the stem cell dissociation; where the final stem cell product will have many of the original cells intact.

Other methods present issues with respect to low yield and cells rupturing, which causes damage to otherwise healthy adipose tissue. Additionally, such methods make it difficult to maintain an aseptic process and are open, which increases the risk of contamination and infection. Therefore, there is a general need in the field for a method of safely and efficiently harvesting regenerative cells and ASCs from adipose tissue, without the use of any enzymes and without altering the structural ability of the adipose tissue for repair or reconstruction.

The following references are incorporated by reference in their entities:

Zuk, P. A., Zhu, M., Ashjian, P., De Ugarte, D. A., Huang, J. I., Mizuno, H., Hedrick, M. H. (2002) titled Human Adipose Tissue Is a Source of Multipotent Stem Cells, and published in *Molecular Biology of the Cell*, 13(12), 4279-4295. doi:10.1091/mbc.E02-02-0105.

Waki, H. & Tontonoz, P. Endocrine functions of adipose tissue. *Annu Rev Pathol* 2, 31-56 (2007).

Dominici, M. et al. Minimal criteria for defining multipotent mesenchymal stromal cells. The International Society for Cellular Therapy position statement. *Cytotherapy* 8, 315-317 (2006).

Hasty, K. A., Stricklin, G. P., Hibbs, M. S., Mainardi, C. L. & Kang, A. H. The immunologic relationship of human neutrophil and skin collagenases. *Arthritis Rheum* 30, 695-699 (1987).

Yeh, A. T., Choi, B., Nelson, J. S. & Tromberg, B. J. Reversible Dissociation of Collagen in Tissues. *J Invest Dermatol* 121, 1332-1335 (2003).

Rose, J. G. Jr., Lucarelli, M. J., Lemke, B. N., Dortzbach, R. K., Boxrud, C. A., Obagi, S., & Patel, S. Histologic comparison of autologous fat processing methods. Ophthalmic plastic and reconstructive surgery, Vol. 22, No. 3, (May-June 2006), pp. 195-200, ISSN1537-2677.

SUMMARY OF THE INVENTION

The present inventive concept remedies the aforementioned problems by providing, according to one aspect of the present disclosure, an adipose-derived stem cell (ASC), regenerative cell and/or regenerative factor processing system, including a tissue extraction device for extracting raw tissue, such as adipose tissue, from a patient, an ASC, regenerative cell and/or regenerative factor isolator, and an implantation device for re-introducing the isolated ASCs, regenerative cells and/or regenerative factors into the patient. The ASC, regenerative cell and/or regenerative factor isolator includes a receptacle configured to receive the adipose tissue from the tissue extraction device, and an ultrasonic generator configured to excite the raw tissue with ultrasonic energy for isolating ASCs, regenerative cells and/or regenerative factors from the raw tissue. The ultrasonic energy has controllable variable duration, frequency and amplitude with energy sufficiently low not to cause cavitation within the raw tissue and subsequent tissue destruction on a large scale. It is foreseen that one or more other types of cells, e.g., cells other than ASCs, that are useful to the regenerative process may be collected without deviating from the scope of the present inventive concept.

The ultrasonic dissociation apparatus and methods of use detailed herein involve using resonant frequencies of cells, cellular structures, cell clusters, collagen fibrils and/or extracellular matrix components with sub-cavitation levels of ultrasonic energy to selectively lyse cells or disrupt extracellular adherence of cells to each other. Ultrasonic energy may be harnessed to cause dissociative vibration or resonance through the entire cell, through multi-cellular clusters, through portions of the cell like a structural element of a cell wall that can be targeted, or through structures that facilitate adherence to the extracellular matrix and to the extracellular matrix itself. This method may also combine ultrasonic dissociation with osmotic pressure to make selected cells more susceptible to dissociation or lysing when exposed to ultrasound.

The ultrasonic dissociation apparatus and methods of use detailed herein overcome the deficiencies of currently utilized methods through the use of variable amplitude ultrasound waves, variable frequencies as well as variable osmotic and hydrostatic pressures and mechanical methods to mechanically dissociate ASCs and/or other factors from surrounding tissue without cavitation and subsequent destruction of adipocytes and tissue components. Yield of the ASCs, regenerative cells and/or regenerative factors is maintained while the potential for damage to the desired ASCs, regenerative cells and/or regenerative factors is decreased due to lower stresses placed upon them during the process. In addition, targeted ultrasonic dissociation allows for specific cell and/or cell cluster and/or structural sizes to be selected for dissociation, preserving the integrity of the original tissue.

The disclosed methods of ultrasonic dissociation are faster, result in a much smaller impact on the host tissue, do not require the use of exogenous dissociating enzymes and the closed system design maintains an aseptic dissociation environment, minimizing the risk of contamination. Also, the disclosed methods can be used in vitro and in vivo to dissociate aggregated clusters of ASCs and/or somatic cells without the use of any digestive enzymes. This preserves the integrity of the cells and contributes to increased survivability of the cells. With targeted ultrasonic dissociation, the factors associated with ultrasound, frequency, wavelength and amplitude can be rigidly controlled and easily reproduced; unlike the way a particular enzyme's activity may vary between lots, manufacturers, employees and/or locations. The end product is a high yield cellular product for use in human and animal research, and in medical and veterinary applications.

Additional aspects, advantages, and utilities of the present disclosure will be set forth in part in the description which follows and, in part, will be obvious from the description, or may be learned by practice of the present disclosure.

The foregoing is intended to be illustrative and is not meant in a limiting sense. Many features and sub-combinations of the present disclosure may be made and will be readily evident upon a study of the following specification and accompanying drawings comprising a part thereof. These features and sub-combinations may be employed without reference to other features and sub-combinations.

BRIEF DESCRIPTION OF THE DRAWINGS

Embodiments of the present disclosure are illustrated by way of example in which like reference numerals indicate similar elements and in which.

DETAILED DESCRIPTION OF THE INVENTION

The following detailed description references the accompanying drawings that illustrate various embodiments of the present disclosure. The illustrations and description are intended to describe aspects and embodiments of the present disclosure in sufficient detail to enable those skilled in the art to practice the present disclosure. Other components can be utilized and changes can be made without departing from the scope of the present disclosure. The following detailed description is, therefore, not to be taken in a limiting sense. The scope of the present disclosure is defined by the appended claims, along with the full scope of equivalents to which such claims are entitled.

I. TERMINOLOGY

In the following detailed description, terminology is used to describe features of the present disclosure. For example, references to terms "one embodiment," "an embodiment," or "embodiments" mean that the feature or features being referred to are included in at least one aspect of the present disclosure. Separate references to terms "one embodiment," "an embodiment," or "embodiments" in this description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments, but is not necessarily included. Thus, the present disclosure may include a variety of combinations and/or integrations of the embodiments described herein. Additionally, all aspects of the present disclosure as described herein are not essential for its practice.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps, or acts are in some way inherently mutually exclusive.

As used herein, "adipose-derived stem cells" or "ASCs" means the heterogeneous population of pluri- and/or multi-potent cells that is found within adipose tissue and/or lipoaspirate, including but not limited to mesenchymal stem cells (MSC), multi-lineage stress-enduring adipose tissue (MuSE-AT), hematopoietic stem cells (HSC), supra-adventitial cells, pericytes and/or others.

As used herein, "regenerative cells" includes ASCs as defined above as well as progenitor cells that are found within adipose tissue and/or lipoaspirate, including but not limited to endothelial progenitor cells (EPC), preadipocytes, vascular progenitors, hematopoietic progenitors, fibroblasts, platelets, adipocytes, osteocytes and/or others.

As used herein, "regenerative factors" includes components of the adipose tissue and/or lipoaspirate that includes but is not limited to all types of collagen, extracellular matrix, fibronectin, growth factors, soluble factors, cytokines, plasma, proteoglycans and/or others.

As used herein, "patient" refers to entities that include but are not limited to humans, animals, plants, fungi, microorganisms and microbes from which ASCs, regenerative cells and/or regenerative factors may be harvested and/or extracted, and/or entities that include but are not limited to humans, animals, plants, fungi, microbes and microorganisms to which the ASCs, regenerative cells and/or regenerative factors may be introduced or transplanted.

As the present disclosure is susceptible to embodiments of many different forms, it is intended that the present disclosure be considered as an example of the principles of the present disclosure and not intended to limit the present disclosure to the specific embodiments shown and described.

II. GENERAL ARCHITECTURE

Figure 1:
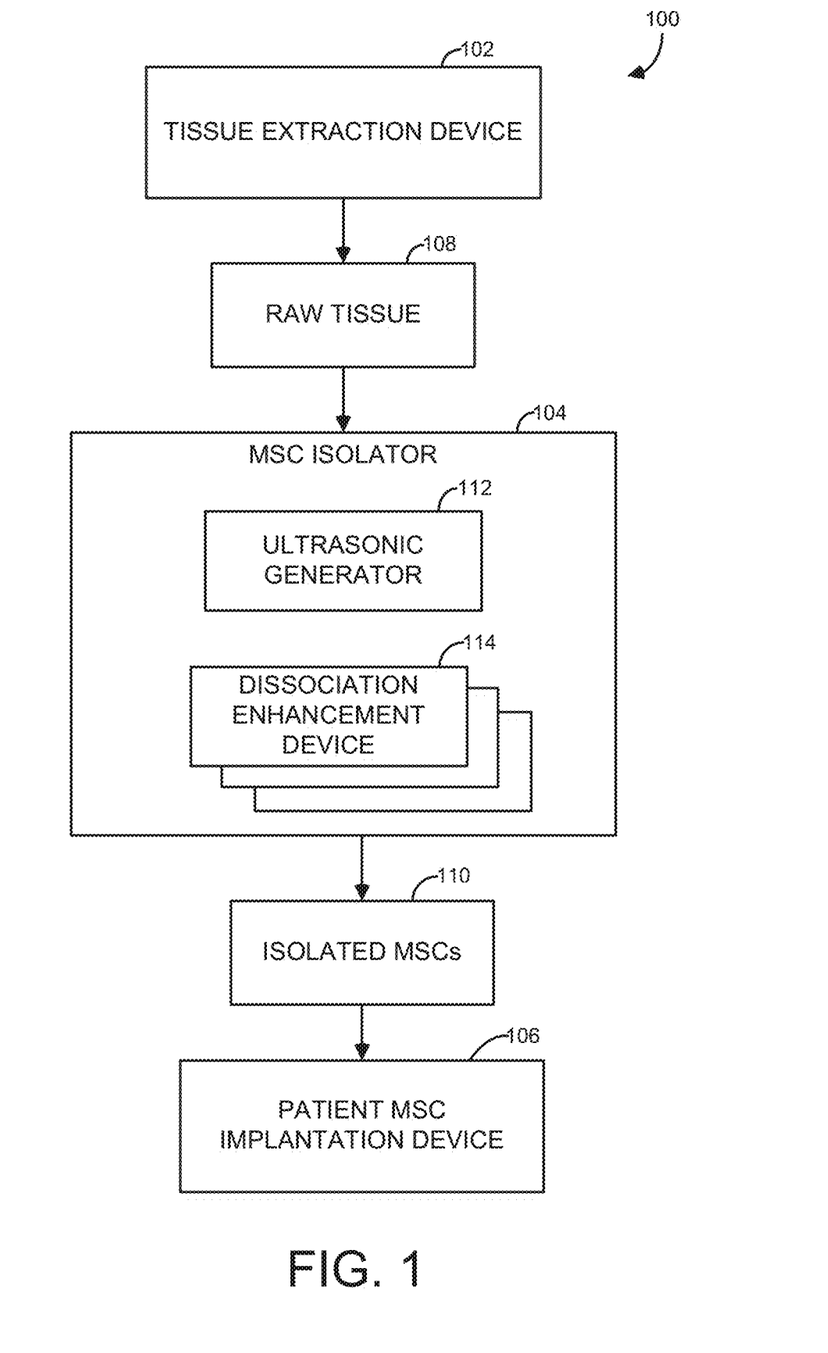
FIG. 1 illustrates an example of an adipose-derived stem cell (ASC), regenerative cell and/or regenerative factor processing system according to one embodiment of the present disclosure.

Embodiments of the present disclosure provide an adipose-derived stem cell (ASC) processing system and methods of use that isolates ASCs, regenerative cells and/or regenerative factors from raw tissue (e.g., lipoaspirate samples) using one or more mechanical processes. While conventional isolation techniques, such as the enzymatic digestion process that incubates raw tissue with an enzyme for a specified period of time, can cause immunological reactions due to the introduction of enzymes derived from bacteria, plant, fungal and/or animal sources, the ASC processing system 100 disclosed herein uses relatively low levels of ultrasonic energy along with one or more other dissociation enhancement processes to dissociate ASCs, regenerative cells and/or regenerative factors in a manner that eliminates the need to utilize enzymes entirely. Additional embodiments provide an ASC isolation device that facilitates extraction of raw tissue (e.g., adipose tissue), isolation of ASCs, regenerative cells and/or regenerative factors from the raw tissue using the aforementioned process, and implantation of the isolated ASCs, regenerative cells and/or regenerative factors back into a patient for one or more treatment purposes.

Research and clinical groups have historically used different procedures to isolate and manipulate ASCs, such as differing the type and concentration of enzymes used, the time and conditions of incubation for adipose tissue digestion, and methods of cell culture. These methodological differences often result in diverse characteristics of the isolated cells, thus yielding varied results. Therefore, the development of a standardized and reproducible method of isolating ASCs, as well as standard techniques for functional characterization, is fundamental to validating cells for its use in therapeutic procedures.

A protocol for functional characterization of ASCs, more specifically mesenchymal stem cells a specific sub-set of ASCs, has been proposed by the International Society for Cellular Therapy (ISCT). According to this proposed protocol, mesenchymal stem cells (MSCs) should be plastic-adherent in standard cultures, express a mesenchymal set of surface molecules, and differentiate into osteoblasts, adipocytes, and chondroblasts in vitro. The detection of a set of surface molecules such as, for example, mesenchymal or ASC surface molecules, as well as the differentiation assays, can be performed on adipose-tissue ASC populations after their isolation in laboratory and will be described in detail herein below. Though the following disclosure is directed in some aspects to MSCs, it is not limited to MSCs. The disclosed principles can be utilized with any cell type falling within the scope of ASCs, as the same is defined herein.

Long-term cultured MSCs maintain their differentiation capacity towards osteo-, chondro-, adipo-, and myo-genic lineages, also expressing MSC markers. Stable phenotypes may be provided after extensive expansion. Nevertheless, conventional adipose-derived MSC processing techniques, such as the enzymatic approach, have not produced in vitro spontaneous transformation of human MSCs under usual conditions of culture.

FIG. 1 illustrates an example of an ASC processing system 100 according to one embodiment of the present disclosure. The system 100 includes a tissue extraction device 102, an ASC, regenerative cell and/or regenerative factor isolator 104, and a patient ASC, regenerative cell and/or regenerative factor implantation device 106. As will be described in detail below, the tissue extraction device 102 extracts raw tissue 108 from a patient, and provides the extracted tissue 108 to an ASC isolator 104, which isolates (separates) ASCs, regenerative cells and/or regenerative factors 110 from the raw tissue 108 using ultrasonic energy provided by an ultrasonic generator 112 and one or more dissociation enhancement devices 114. Thereafter, the isolated ASCs, regenerative cells and/or regenerative factors may be re-introduced into the patient, for example for performing one or more medical treatment regimens, using the patient ASC, regenerative cell and/or regenerative factor implantation device 106.

The raw tissue 108 may be obtained from any suitable tissue of the patient, such as bone marrow. In one embodiment, the raw tissue 108 is obtained from adipose tissue that is extracted from the patient. Although ASCs can be isolated from different tissues, adipose tissue has been proposed as an alternative to bone marrow tissue, since adipose tissue is abundant, easily-harvested by liposuction, and adipose tissue MSCs (like bone marrow MSCs), can differentiate towards mesenchymal lineages.

Various techniques have been developed for harvesting adipose tissue and preparing it for research and clinical use. In one embodiment, the tissue extraction device 102 extracts adipose tissue using a liposuction process. Liposuction can be performed using standard or vibro-assisted techniques.

Vibro-assisted liposuction may reduce the duration of surgery because of its relatively large aspiration rate. The ASCs may be able to be isolated from lipoaspirates harvested by standard or vibro-assisted techniques, using ultrasonic energy or various osmotic processes. In some cases, the quantity of ASCs obtained from vibro-assisted lipoaspirate samples may be superior to that obtained from more conventional techniques, with no substantial differences in adhesion or proliferation in culture.

When taking into account the isolation of ASCs with high cell quality, the use of a defined method of tissue harvesting and preparation can be important. Centrifugation of adipose tissue harvested by liposuction has been used, as it is one of the preferred methods of adipose tissue processing for soft tissue augmentation.

Elements of the extracellular matrix, such as collagen, may be induced to dissociation by means of the introduction of an agent that affects the osmotic pressure of the suspension or tissue. The temporary dissociation of collagen can facilitate the ASC extraction process as well as the collection of microstructures of ASCs and extracellular matrix.

In one embodiment, the extracted raw tissue 108 may be centrifuged and/or decanted prior to insertion in the ASC, regenerative cell and/or regenerative factor isolator 104. For example, the raw tissue (e.g., lipoaspirates) may be prepared by centrifugation (e.g., 1200× gravity (g) for 3 minutes) and decantation (e.g., 30 minutes under the action of gravity). In some cases, however, centrifuged raw tissue may provide a lower yield of isolated ASCs. Moreover, centrifuged ASCs may be less capable to proliferate in vitro, probably due to the centrifugation forces suffered by cells in the raw tissue 108. Also, centrifuged samples showed a fraction of cells in the bottom of the syringe, in the pellet, which were not identified in decanted samples. This fraction had a significant quantity of MSCs.

Possible architectural alterations of adipose tissue caused by these methods may be quantified based on the degeneration of adipocytes, staining tissue histological sections with hematoxilin & eosin or with antibodies against perilipin, an abundant protein in the adipocyte cytoplasmic membrane. Another histological quantification has shown that decanted samples had twice the quantity of intact adipocytes as compared to centrifuged and washed samples. It has been observed that the adipose tissue resulted from centrifuged lipoaspirate samples contained mainly adipocytes with disrupted membranes and general extracellular matrix disruption, whereas decantation maintained the adipocytes' integrity.

In some cases, reducing centrifugation forces will improve ASC recovery on centrifuged lipoaspirate samples. For example, a centrifugal force of approximately 1200 g may be used for obtaining good short-term and long-term results in adipose transplantation. Various speeds and time intervals for centrifugation may be used, but a destruction of living fat may result histologically. Thus, centrifugation of adipose tissue harvested by liposuction may have a negative effect on tissue architecture and morphology, losing its stem cell content, as ASCs are lost in the pellet, as well as on the yield and quality of ASCs subsequently isolated from the resulting tissue. On the other hand, decantation resulted in relatively little harm to tissue structure and allows a substantial quantity of cells isolated, with a good proliferation rate and morphology.

The future of autologous fat transplantation seems to lie in stem cell research, specifically in adipose ASCs. However, the use of adipose ASCs raises numerous concerns, including the choice of harvesting and processing, cell isolation, and culture. Scientific research is emerging to address these issues. Membranes of adipocytes were disrupted when adipose tissue was submitted to forces generated during centrifugation, probably due the fact that adipocytes are very fragile cells with only a thin cytoplasmic envelope surrounding large fat droplets. On the other hand, ASCs are smaller and more resilient, which makes them more practical to work with than adipocytes.

The ASC, regenerative cell and/or regenerative factor isolator 104 isolates ASCs, regenerative cells and/or regenerative factors 110 from the raw tissue 108 using ultrasonic energy provided by an ultrasonic generator 112 and one or more dissociation enhancement devices 114. The ultrasonic energy is maintained at a level sufficiently low not to cause cavitation of the ASCs, which could potentially damage their cell structure. In one embodiment, the frequency of the ultrasonic energy is selected to resonate in the ASCs, regenerative cells and/or regenerative factors based upon their sizes. For example, the ultrasonic generator 112 may slowly cycle through frequencies for a range of cellular sizes and clusters from small cells averaging 50 micrometers ($\mu$m) to larger cells averaging 100 $\mu$m, which may target the adipocytes, and also to larger cellular clusters over 100 $\mu$m and extending to several millimeters in size. In another embodiment, the ultrasonic generator 112 may use beat frequencies and/or a manual control and/or programmatic control to modulate the amplitude to avoid cavitation and thus destruction of the ASCs. Additionally, controlled use of one or more osmotic processes may be used to dissociate or selectively weaken the raw tissue 108 to aid in releasing ASCs from the raw tissue 108.

Conventional techniques for isolating ASCs from adipose tissue include an enzymatic digestion process that includes the steps of digestion, washing, centrifugation, and red blood cell lysis. Adipose tissue from lipoaspirate samples is incubated with collagenase for a specified period of time (e.g., approximately 1-2 hours). Next, the mixture is washed, and centrifuged to separate the floating adipocytes from the pelleted stromal ASCs. The pelleted stromal ASCs are then incubated with a red blood cell lysis solution and centrifuged one more time. This enzymatic digestion process generates tissue fragments that may then be removed (before cell plating) through a sieve (e.g., 100-150 $\mu$m nylon mesh). Irrespective of the source of tissue, enzymatic digestion is time-consuming and expensive, especially when applied to large volumes of tissue. Decreased cell viability due to lytic activity may also present a problem with this method.

Embodiments of the present disclosure provide ASC, regenerative cell and/or regenerative factor isolation from lipoaspirate samples using various mechanical tissue dissociation techniques. The population of MSCs derived using the dissociation enhancement techniques has been shown to be positive for mesenchymal surface markers, such as cluster of differentiation (CD) 90 and CD105. They may also be positive for CD34, which is reported only in adipose tissue-derived MSCs. They also were able to accumulate lipid droplets, deposit extracellular calcium and cartilage extracellular matrix, under specific stimuli for each differentiation event. Their proprieties support their use for diverse therapeutic applications. Techniques used on these assays will be described in detail below.

In general, CD antigens are proteins expressed on cell membranes. They are commonly used as cell markers, allowing cells to be defined based on which molecules are present on their surface. However, CD antigens are not merely markers of cells. They usually act as receptors or ligands which initiate a signal cascade, being responsible for different cell behaviors. Besides cell signaling, some CD antigens have different functions, like cell adhesion. A nomenclature may be used to describe different monoclonal antibodies against specific antigens, using the term CD plus a number. For example, an antibody that detects a specific glycoprotein on the surface of T helper lymphocytes is named CD4.

Embodiments of the ASC, regenerative cell and/or regenerative factor processing system 100 isolate ASCs, regenerative cells and/or regenerative factors from lipoaspirate samples and provide a relatively high quantity of cells with reduced time and costs relative to conventional techniques. While the enzymatic digestion process for adipose tissue requires at least four main steps, the ASC, regenerative cell and/or regenerative factor isolation process may use fewer steps, such as: (i) dissociation of adipose tissue concomitantly with red blood cell lysis, and (ii) centrifugation. There are little or no visible tissue fragments, and it may not be necessary to the filter the cell suspension. The ease of mechanical digestion reduces considerably both time and cost, and does not significantly interfere with cell viability. Furthermore, an ASC culture derived from the ASC, regenerative cell and/or regenerative factor isolation process may provide a higher yield of cells than the enzymatic digestion process after primary culture.

In addition to providing advantages in time and cost, the ASC, regenerative cell and/or regenerative factor isolation process provides enhanced reproducibility, making it useful for relatively large volumes. Additionally, the ASC, regenerative cell and/or regenerative factor isolation process may provide for cryopreservation of freshly-isolated ASCs. ASC isolation using the enzymatic digestion process that have been cryopreserved using $Me_2SO$ as the cryoprotective agent have a density of $10^6$ cells/milli-liter (mL), whereas cryopreservations of MSCs isolated using the MSC isolation system 100 have higher densities (e.g., approximately a factor of 10). The centrifugation step in both the enzymatic digestion process and ASC isolation process is used to separate ASCs from adipose tissue fragments, oil, and debris. Resulting pellets are re-suspended and seeded into culture dishes in a suitable cell culture medium containing, for example, fetal bovine serum and antibiotics. Only the pellets obtained by ASC, regenerative cell and/or regenerative factor isolation method can be alternatively re-suspended in fetal bovine serum supplemented with 10 percent (%) dimethylsulfoxide (DMSO) for cryopreservation and storage at −196° C. until thawing.

Cryopreservation may be useful because it reduces labor costs and avoids possible loss of cell viability and senescence after long-term cultures. Another approach to isolate ASCs is based on a primary explants culture process. A small fragment of any tissue that adheres to the growth surface will usually give rise to an outgrowth of cells. Historically, most studies of adipose tissue metabolism were carried out by the explants culture process. Recently, the explants culture process has been shown to yield adipose tissue fragments that could adhere onto the growth surface of culture flasks after plating; MSCs migrated from the explants reached confluence after a period of time. Following in vitro expansion, this population of MSCs may be induced into adipogenic, osteogenic, and chondrogenic lineages, which may provide multipotency. Nevertheless, despite the cost advantages of the explants culture process, the techniques that are employed to adhere successfully adipose tissue fragments onto the surface of flasks depend exclusively on the manual skills of the laboratory technician, which effectively makes it difficult to reproduce with any sufficient regularity.

A celution cell-processing device is a particular type of medical device used for processing adult adipose tissue stem cells for autologous re-implantation or re-infusion, and is currently being used in cosmetic & reconstructive surgery in Europe and Japan, but is not yet available in the United States due to restrictions by the U.S. Food & Drug Administration (FDA). This system provides access to adipose stem cells by automating the extraction, washing, and concentration of a patient's own cells for immediate use.

The suctioned adipose tissue is introduced into the celution cell-processing device and is enzymatically digested into a single-cell suspension, which contains a combination of ASCs, endothelial progenitor cells, and other adipose tissue stromal cells. The cell suspension is washed and all lipid-laden adipocytes and matrix fragments are separated from the cell suspension. The procedure is performed in a closed-circuit arrangement, thus reducing the chance of cell suspension contamination, such as by fungus and bacteria. This automated closed-circuit arrangement would facilitate research and be conducive for bedside use. However, the celution cell-processing device uses an enzymatic procedure to obtain a cell suspension, which can cause immunological reactions caused by enzyme-derived animal proteins and destruction of adipocytes and extracellular structures and collagen.

The ability to isolate, expand, cryopreserve, and differentiate ASCs may be important aspects in the development of cell therapy approaches for therapeutic proposes for chronic, degenerative diseases, as well as for their application in plastic or reconstructive surgery. It may be that inconsistent data about therapeutic potentials of ASCs are a result from different ASC cell culture acquisition practices. Embodiments of the present invention provide a solution to this problem by providing an ASC, regenerative cell and/or regenerative factor isolation system 100 that isolates and processes ASCs with a greater level of consistency that what has heretofore been provided.

The isolated ASCs may be implanted back into the patient to perform one or more forms of treatment using the patient implantation device 106. The use of adipocytes and ASCs for tissue repair and regeneration can follow at least two different procedures. The liposculpture uses the freshly harvested adipose tissue, generally obtained by liposuction. The tissue is frequently harvested, processed and re-injected during the same surgical procedure. ASCs can be introduced simultaneously, and the tissue processing must take into account their viability and their capacity to functionally integrate into the tissue where they are implanted.

Alternatively, ASCs can be harvested and expanded in vitro, in order to reach the required cell number, and used subsequently for filling or repair of different tissues, such as dermis, connective tissue, bone and associated tissues, as well as blood vessels in repair of both peripheral or cardiac tissue ischemia. In these cell therapies, the implantation of cells may lag behind the harvesting for several days or weeks.

Additionally, ASCs can be harvested and transformed in vitro into induced pluripotent stem cells (iPSC). The iPSCs can then be differentiated along all lineages of endo-, ecto- and meso-dermal origins to engineer or regenerate and/or repair tissue and/or organs. The iPSCs may be used in cloning applications, cellular rejuvenation and/or gene repair.

Autologous ASCs, such as those derived from bone marrow or adipose tissue, can be used clinically for regenerative cell therapy or for tissue engineering when isolated in a reproducible manner and in sufficient quantities. They may be transplanted immediately without expansion or differentiation, or they may be cultured to undergo expansion and differentiation. The expansion and differentiation steps may provide increased cell number, purity, and maturity, but do so at a cost. This cost can include one or more of loss of cell function due to cell passaging, increased monetary cost, and increased risk of contamination of cells with environmental microorganisms during culture.

Liposuction surgery often generates large volumes of samples. There is need for alternative methods in which a population of active cells with increased yield can be prepared rapidly and reliably, and whereby the need for post-extraction manipulation of the cells can be reduced or eliminated. Embodiments of the ASC, regenerative cell and/or regenerative factor isolation system 100 provide for dissociation of adipose tissue in order to release ASCs from it in a manner suitable for direct placement into a recipient or for direct cryopreservation in a laboratory.

The possibility of cryopreservation of freshly-isolated ASCs abrogates culture-associated changes found in cells after prolonged expansion, and provides the possibility of generating extemporaneously a large stock of cells (e.g., an ASC bank) using the ASC isolation system 100. Once cryopreserved, ASCs can be thawed as the need arises, without loss of cell viability and functionality. Autologous fat grafts are an important procedure for soft-tissue filling. But, it is important to avoid resorption of transplanted fat, which is undesirable.

Results show that centrifugation, while cleaning adipose tissue of potentially-harmful substances, yields adipose tissue which is not only devoid of viable adipocytes but also has a diminished percentage of ASCs. Taken together, the long term graft of the implanted centrifuged adipose tissue is less probable, and the implant resorption naturally occurs with clearance of non-viable organic components introduced into the receptor site. In contrast, decantation acceptably separated the supranatant layer of adipose tissue from the oily and sero-sanguinous liquids (infranatant layer), besides preserving the integrity of adipose tissue and number and viability of adipocytes and ASCs.

Adipose tissue harvesting and processing techniques may play an important role in the viability and integrity of adipose tissue, and also on the densities of ASCs obtained. For example, a long-term graft is reached mainly by angiogenesis; ASCs enhance local angiogenesis by differentiation events and secretion of angiogenic factors. To overcome drawbacks of autologous lipoinjection, a strategy is provided, which is based on ASC association with autologous fat and extracellular matrix working as a scaffold. This strategy may result in long-term retention of the fat graft. Embodiments of the ASC isolation system 100 may provide for dissociation of adipose tissue in a manner that may not require enzymatic treatment, while generating a cell suspension devoid of (or mostly devoid of) both tissue debris and enzyme waste. It may be possible to perform the ASC isolation in which a cell suspension enriched with ASCs can be injected simultaneously with fresh adipose tissue and extracellular matrix scaffold. This association (e.g., cell suspension enriched with ASCs and fresh adipose tissue from decanted lipoaspirate sample) could be used for volume restoration of facial depressions caused by sequelae of trauma and tumors.

Alternatively, ASCs can be harvested with elements of collagen and the extracellular matrix, providing additional structural components small enough to maintain in suspension and pass through a syringe for injection. The ASCs may still be attached to elements of the extracellular matrix. These constitute regenerative microstructures which can be injected and implanted directly into treatment areas such as cartilage or adipose tissue.

Figure 2A:
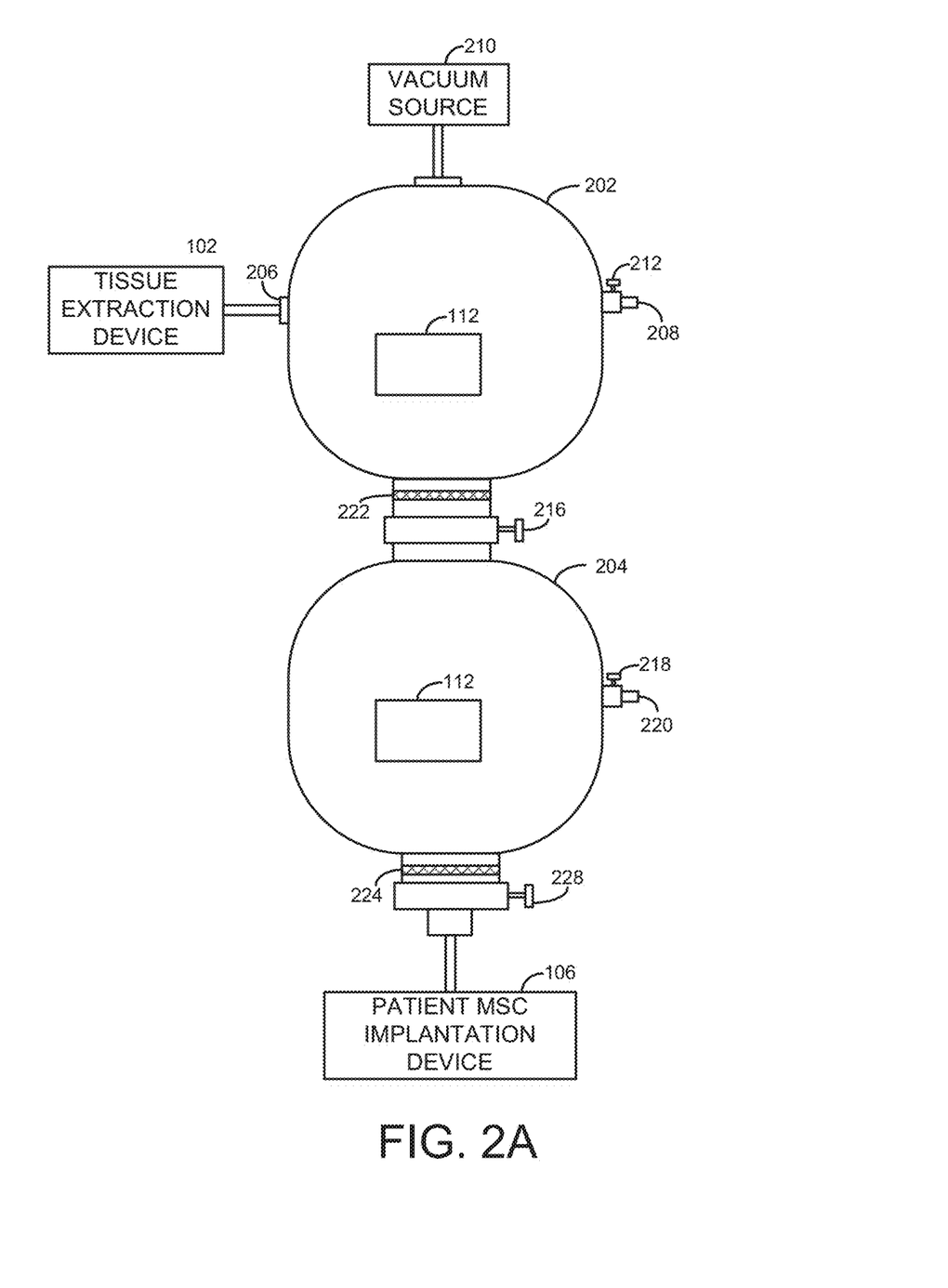
FIGS. 2A-2C illustrate an example of an ASC, regenerative cell and/or regenerative factor isolator and tissue extraction devices that may be used to isolate ASCs, regenerative cells and/or regenerative factors from raw tissue according to one embodiment of the present disclosure.
Figure 2B:
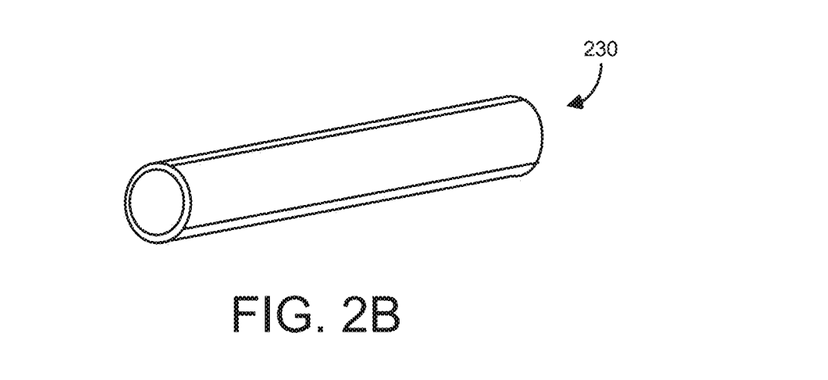
Figure 2C:
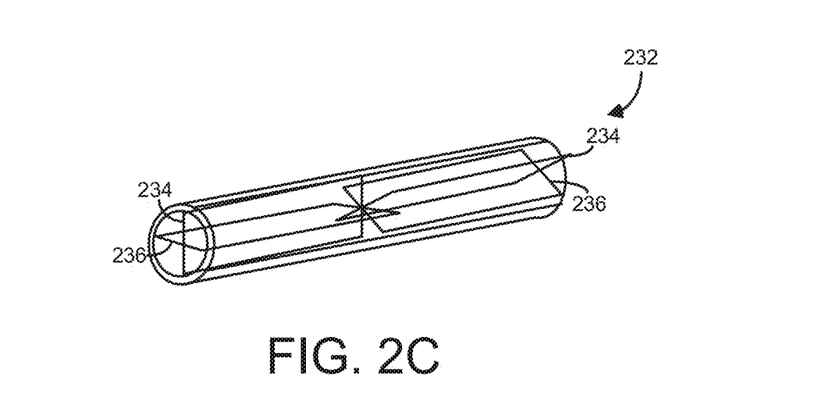

FIGS. 2A-2C illustrate an example of an ASC, regenerative cell and/or regenerative factor isolator 104a and tissue extraction device that may be used to isolate ASCs from raw tissue 108 according to one embodiment of the present disclosure. The ASC isolator 104a includes a first chamber 202 and a second chamber 204. The first chamber 202 has a volume of approximately 200 cc and includes a raw tissue entry port 206 for receiving raw tissue 108 from the tissue extraction device 102, a suction port 208 that may be fluidly coupled to a vacuum source 210 for providing a vacuum within the first chamber 202, and a valve 212 configured with a luer lock or other type of port 214 for entry of one or more additional substances into the first chamber 202. The second chamber 204 has a volume of approximately 200 cc and is in fluid communication with the first chamber 202 via a release valve 216, and also includes a valve 218 configured with a luer lock or type of port 220 for entry of one or more additional substances into the second chamber 204. [NTD: highlighted reference numerals are not shown in the Figures]

As shown, the first chamber 202 includes a large pore filter (sieve 222) with a mesh approximating 200 micrometers, while the second chamber 204 includes a micropore filter 224 with a mesh approximating 35 micro-meters. It should be understood, however, that any size mesh may be used. Furthermore, the large pore filter 222 and the micropore filter 224 may be omitted, if not needed or desired.

The large pore filter 222 and micropore filter 224 generally form one example of dissociation enhancement devices 114 that may be used to enhance dissociation of ASCs from the raw tissue 108. Embodiments contemplate that other types of dissociation enhancement devices may be implemented. For example, a dissociation enhancement device 114 that performs hypo-osmotic lysis targeting of erythrocytes and/or adipocytes may be implemented. As another example, a temperature-lowering device that lowers the temperature of the raw tissue 108 above the freezing point (32 degrees Fahrenheit) may be used. As another example, a pressurizing device that increases the internal pressure of the first chamber 202 and/or second chamber 204 may be implemented. As yet another example, dissociation enhancement devices 114 that provide vortex and agitation may be implemented. As another example, dissociation enhancement devices 114 may be implemented that lower or raise the osmotic pressure of the suspension or tissue, and/or, lower or raise the pH level of the raw tissue 108 via the luer locks or other types of ports 212 and 218. As yet another example, dissociation enhancement devices 114 may be implemented that cause mechanical disruption, such as provided by spinning elements (e.g., blades).

The first chamber 202 and the second chamber 204 are each configured with an ultrasonic generator 112 to impart ultrasonic energy into the raw tissue 108, although, in other embodiments, only the first chamber 202 and/or the second chamber 204 may be implemented with an ultrasonic generator 112.

The first chamber 202 is fluidly-coupled to a tissue extraction device 102, such as a cannula, from which raw tissue 108 (e.g., adipose tissue) may be extracted from a patient using suction provided by the vacuum source 210. The first chamber 202 provides an initial isolation process for dissociating ASCs from the raw tissue 108, while the second chamber 204 provides a second isolation process using the output of the initial isolation process provided by the first chamber 202. The second chamber 204 also includes a release valve 228 to release isolated ASCs 110 from the second chamber 204.

FIGS. 2B and 2C illustrate example tissue extraction devices that may be used with the MSC isolator 104a according to the teachings of the present disclosure. In particular, the tissue extraction devices of FIGS. 2B and 2C are cannulas 230 and 232 that may be particularly adapted for extraction of adipose tissue from a patient. The cannula 230 of FIG. 2B is a concentric design in which its orifice is cylindrically-shaped. Like the cannula 230 of FIG. 2B, the cannula 232 of FIG. 2C includes a cylindrically-shaped orifice, but also includes internally mounted blades 234 and 236 that break up the raw tissue 108 as it is extracted from the patient. Additionally, multiple sections of the blades may be provided to enhance the dissociation process. That is, a first section of blades 234 are arranged in a cross pattern, perpendicular to one another, while a second section of blades 236 are also arranged in a cross pattern, which is perpendicular to one another. The second section of blades 236, however, are oriented an additional 45 degree angle relative to the first section of blades 234 such that dissociation of the raw tissue 108 may be enhanced.

Figure 3:
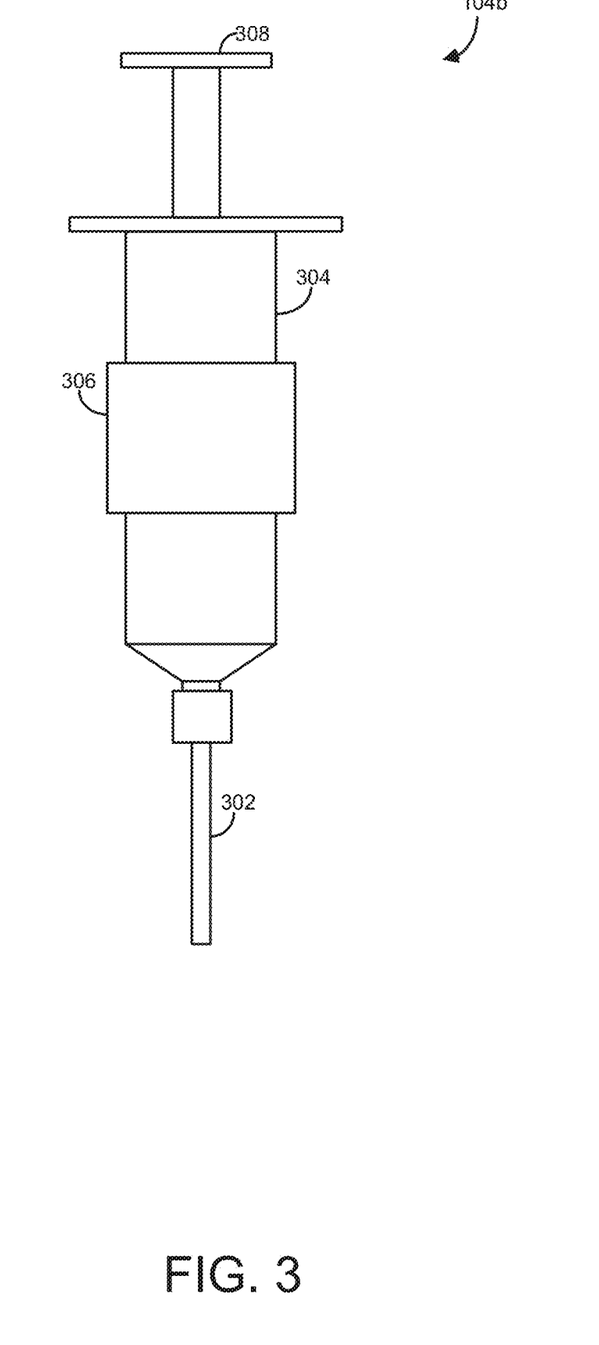
FIG. 3 illustrates another example of an ASC, regenerative cell and/or regenerative factor isolator according to one embodiment of the present disclosure. [NTD: this figure is labeled as "FIG. 1" in the drawings, not "FIG. 3."]

FIG. 3 illustrates another example of an ASC, regenerative cell and/or regenerative factor isolator 104b according to the teachings of the present disclosure. The ASC, regenerative cell and/or regenerative factor isolator 104b includes a tissue extraction device 302, a chamber (e.g., barrel of the syringe) 304, and an ultrasonic generator 306 physically coupled to the chamber 304. In general, the ASC, regenerative cell and/or regenerative factor isolator 104b differs, however, in that the chamber 304 comprises a syringe having a piston 308 that may be physically manipulated for sucking raw tissue 108 from the patient. As shown, the ultrasonic generator 306 may be physically coupled to the chamber 304, such as, for example, on the outer surface of the chamber, for imparting ultrasonic energy into the raw tissue matrix. Although not shown, the syringe may also be configured with one or more dissociation enhancement devices, such as those described above with respect to FIGS. 2A-2C.

Although FIG. 3 describes one example of an ASC, regenerative cell and/or regenerative factor isolator 104b that may be used for dissociating ASCs, regenerative cells and/or regenerative factors, other embodiments contemplate that other ASC, regenerative cell and/or regenerative factor isolators may be implemented and/or that the ASC, regenerative cell and/or regenerative factor isolator 104b may be used in different ways without departing from the spirit and scope of the present disclosure. For example, it is contemplated that the ASC, regenerative cell and/or regenerative factor isolator 104b of FIG. 3 may be used to extract raw tissue from a patient and perform an initial isolation process. Thereafter, the resulting matrix from the initial isolation process may be transferred to the ASC, regenerative cell and/or regenerative factor isolator 104a of FIGS. 2A-2C to perform additional isolation processes for further dissociation of ASCs, regenerative cells and/or regenerative factors from the raw tissue.

Figure 4:
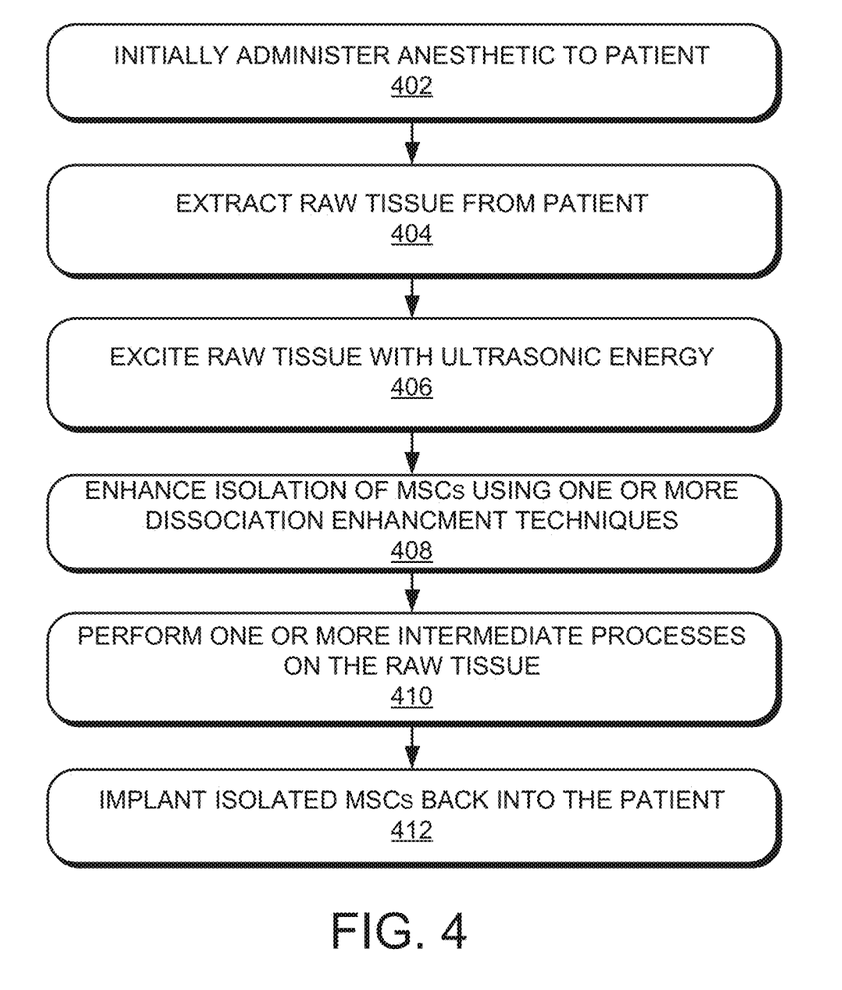
FIG. 4 illustrates an example of a process that may be performed using either the ASC isolator of FIGS. 2A-2C or the ASC, regenerative cell and/or regenerative factor isolator of FIG. 3 to isolate ASCs, regenerative cells and/or regenerative factors from raw tissue according to one embodiment of the present disclosure.

FIG. 4 illustrates an example of a process that may be performed using either the ASC isolator 104a of FIGS. 2A-2C or the ASC, regenerative cell and/or regenerative factor isolator 104b of FIG. 3 to isolate ASCs, regenerative cells and/or regenerative factors from raw tissue 108 according to the teachings of the present disclosure. In step 402, the patient may be optionally administered with an anesthetic, such as a tumescent local anesthetic, for reduction of pain.

In step 404, the tissue extraction device 102 is used to extract raw tissue 108 from the patient using negative pressure as provided by either a vacuum source 210 (FIG. 2B) or from negative pressure provided by the piston 308 of a syringe (FIG. 3). A micro-cannula, such as that described above with respect to FIG. 2B or 2C, and having a diameter of approximately 2 to 3 millimeters is inserted into the patient. The cannula may also include blades 234 and 236 to aid in mincing the raw tissue 108 to loosen its extracellular matrix. In one embodiment, a twin-cannula liposuction technique and/or a water assisted liposuction technique can be administered to retrieve the raw tissue 108 to increase the loosening of the extracellular matrix through its mechanical action. Additionally, ultrasonic energy may be provided to the patient where the raw tissue is drawn and/or to the cannula itself to loosen the extracellular matrix.

In step 406, the raw tissue 108 is excited with ultrasonic energy to isolate the ASCs, regenerative cells and/or regenerative factors from the raw tissue 108. In one embodiment, the amplitude or level of ultrasonic energy is maintained at a sufficiently low level to not cause cavitation of the tissue. To this end, the raw tissue 108 may be excited with ultrasonic energy that slowly cycles through resonant frequencies of the ASCs, regenerative cells and/or regenerative factors, and/or use beat frequencies and/or other means to modulate the amplitude to avoid cavitation (and thus destruction) of the ASCs, regenerative cells and/or regenerative factors. The duration, amplitude and frequency may be varied to target cells and/or cellular structures and/or collagen fibrils and/or extracellular matrix either manually or programmatically controlled through hardware or software.

In step 408, the dissociation of the ASCs, regenerative cells and/or regenerative factors from the raw tissue 108 is enhanced using one or more dissociation enhancement techniques. Examples of such techniques include filtering using a sieve, hypo-osmotic targeting and/or lysing of erythrocytes and/or adipocytes, lowering the temperature of the raw tissue 108 above the freezing point (e.g., 32 degrees Fahrenheit), increasing the internal pressure of the raw tissue 108, lowering or raising the osmotic pressure of the suspension or tissue 108, providing vortex and agitation, lowering or raising the pH level of the raw tissue 108, or causing mechanical disruption (such as provided by spinning elements (e.g., blades). The dissociation may be performed before, during, and/or after the raw tissue 108 is excited with the ultrasonic energy.

In step 410, one or more intermediate processes may be performed on the raw tissue 108. The intermediate processes may be performed prior to, concurrently with, or after either ultrasonic excitation and/or administration of one or more enhanced dissociation techniques. For example, an intermediate process may be performed after the raw tissue 108 is excited with ultrasonic energy and before one or more dissociation enhancement techniques are applied. One example of an intermediate process includes incubating the raw tissue 108 at a specified temperature (e.g., 37 degrees Celsius) and for a specified period of time (e.g., 15 minutes). Another example of an intermediate process includes centrifugation at a specified speed (e.g., 900 g) and for a specified period of time (e.g., 15 minutes). Another example of an intermediate process includes washing the raw tissue 108. Another example of an intermediate process includes decanting of raw tissue 108 for a specified period of time. Another example of an intermediate process includes a reversible dissociation of collagen through a hyperosmotic agent 108. The collagen may be resized into smaller, microscopic clusters through dissociation enhancement such as spinning blades 114. Yet another example of an intermediate process includes re-suspending the purified ASCs, regenerative cells and/or regenerative factors following their isolation from the raw tissue 108.

In step 412, the isolated ASCs, regenerative cells and/or regenerative factors 110 are implanted back into the patient to perform one or more treatment regimens. In one embodiment, the isolated ASCs 110 may be cryopreserved for use at a later time.

ASCs isolated in conjunction with collagen and extracellular matrix microstructures can be removed during the enhancement process to be implanted back into the patient.

The process as described above may be repeated to isolate additional ASCs, regenerative cells and/or regenerative factors from the same patient or from a different patient. Nevertheless, when isolation of further ASCs, regenerative cells and/or regenerative factors are no longer needed or desired, the process ends.

Although FIG. 4 describes one example of a process that may be performed by the ASC processing system 100 for isolating ASCs, regenerative cells and/or regenerative factors from raw tissue, the features of the disclosed process may be embodied in other specific forms without deviating from the spirit and scope of the present disclosure. For example, the ASC processing system 100 may perform additional, fewer, or different operations than those operations as described in the present example. As another example, the steps of the process described herein may be performed by a device other than the ASC, regenerative cell and/or regenerative factor isolator 104b of FIGS. 2A-2C, or the ASC, regenerative cell and/or regenerative factor isolator 104b of FIG. 3.

Adipose tissue obtained from a liposuction or a "tummy tuck" may be compressed and excited with vibrational energy to induce liquefaction and subsequent dissociation of ASCs, regenerative cells and/or regenerative factors for selective capture through stages of micropore filters. For instance, an electronic device may be used to apply pressure to the tissue and/or cells and/or cell clusters, e.g., rollers or compressors on each side of the tissue and/or cells and/or cell clusters. An ultrasonic energy generator may be attached to the device to expose the tissue and/or cells and/or cell clusters to ultrasonic energy while pressure is being applied to the tissue and/or cells and/or cell clusters within the device. It is foreseen that the pressure may be applied to a bag or container in which the tissue and/or cells and/or cell clusters pass to maintain aseptic conditions. The tissue and/or cells and/or cell clusters can then be passed or pumped through a filter or sieve for capturing.

Figure 5A:
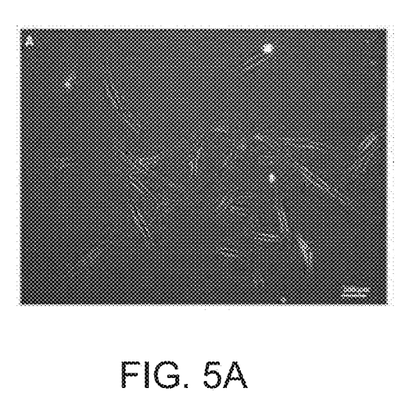
FIGS. 5A and 5B illustrate example results of an ASC culture isolated by the ASC, regenerative cell and/or regenerative factor processing system according to one embodiment of the present disclosure.
Figure 5B:
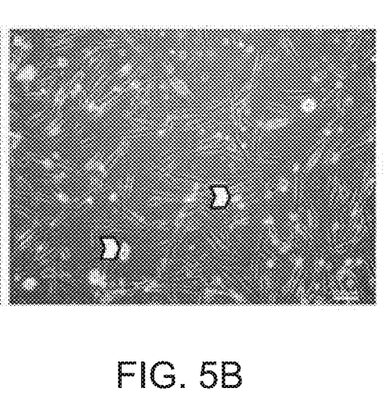

FIGS. 5A and 5B illustrate example results of an MSC culture isolated by the ASC processing system 100. A standardized protocol (e.g., procedure) for the culturing of human adipose tissue MSC and other microbiological quality control procedures was established. Standards for the culture system included the use of alphaMEM (without nucleotides) containing 10% fetal bovine serum selected for cell growth, 100 U/mL penicillin, and 100 µg/mL streptomycin. After isolation, cultures of cells (approximately $10^5$ cells/cm$^2$) were maintained at 37° C. in a humid atmosphere containing 5% $CO_2$. A subset of plated cells could adhere to the culture dish, developing a spindle shape morphology, as shown in FIG. 5A.

Non-adherent cells were removed by washing 24 hours after plating. The medium was changed every 3 to 5 days for proliferation until cells reached pre-confluence; 90% of the culture area was covered by cells approximately 10 to 15 days after plating, as shown in FIG. 5B. Adherent cells were detached with 0.78 mm EDTA and 0.125% trypsin, and cell suspension was centrifuged 400 gravities (g) for 7 minutes.

For cell expansion, cells were re-plated into culture dishes (approximately $10^4$ cells/cm$^2$). This procedure was considered to be 'one passage'. Typical morphology of proliferating cells can be visualized during cell expansion when the cultivation conditions are adequate, as shown by the arrows of FIG. 5B. Cells isolated by the mechanical MSC isolation process maintained the ability to proliferate and the fibroblastic morphology even after 10 passages. No stress actin bundles were visualized.

For MSC cryopreservation, an MSC cell suspension was centrifuged at 400 g for 7 minutes and the pellet was re-suspended in cryopreservation medium consisting of 90% fetal bovine serum and 10% DMSO (dimethyl-sulfoxide). This cell suspension was distributed in cryotubes in the ratio of approximately $10^6$ to $2\times10^6$ cell/tube. Cell freezing was performed for 24 hours in a –70° C. freezer. The cryotubes were then transferred to the gas phase of liquid nitrogen (–196° C.) for long-term storage. Analyses carried out after thawing showed that cells maintained their typical fibroblastic morphology and high viability. The ability to differentiate into mesodermal (adipogenic, osteogenic and chondrogenic) lineages was also attested.

The description above includes example systems, methods, techniques, instruction sequences, and/or computer program products that embody techniques of the present disclosure. However, it is understood that the described disclosure may be practiced without these specific details.

IV. CONCLUSION

The present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intent of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:
1. An adipose-derived stem cell processing device comprising:
   a first chamber for receiving and containing raw tissue;
   an ultrasonic generator configured with the first chamber and configured to induce liquefaction of the raw tissue by exciting the raw tissue at sub-cavitation energy-levels and at the resonant frequency of cells, cellular structures, cell clusters, collagen fibrils and/or extracellular matrix components;
a second chamber that is fluidly-coupled to the first chamber via a valve; and
a filter configured between the first chamber and the second chamber.

2. The processing device of claim 1, wherein the first chamber comprises a bag.

3. The processing device of claim 1, wherein the raw tissue is received using negative pressure provided by a vacuum source.

4. The processing device of claim 1, wherein the raw tissue is received from a cannula.

5. An adipose-derived stem cell processing method comprising:
extracting raw tissue from a patient and passing it to the device of claim 1;
inducing liquefaction of the raw tissue by exciting it with ultrasonic energy at sub-cavitation energy-levels and at the resonant frequency of cells, cellular structures, cell clusters, collagen fibrils and/or extracellular matrix components; and
isolating ASCs from the raw tissue.

6. The method of claim 5, further comprising dissociating the stem cells by performing at least one of: filtering using a sieve, hypoosmotic lysis targeting of erythrocytes and/or adipocytes, introduction of hyperosmotic or hypoosmotic agents to induce dissociation of collagen, lowering the temperature of the raw tissue, increasing the internal pressure of the raw tissue, providing vortex and agitation, lowering or raising the osmotic pressure of the suspension or tissue, lowering or raising the pH level of the raw tissue, or causing mechanical disruption using blades.

7. The method of claim 5, wherein the first chamber comprises a bag and pressure is applied to the bag during the excitation of the raw tissue.

8. The method of claim 5, further comprising cycling through a range of durations, frequencies and amplitudes according to the size of the cells, cellular structures, cell clusters, collagen fibrils and/or extracellular matrix components.

9. The processing system of claim 1, further comprising one or more dissociation enhancement devices configured to enhance dissociation of the stem cells from the raw tissue, wherein the one or more dissociation enhancement devices are configured to perform at least one of: filtering using a sieve, hypo-osmotic targeting of erythrocytes and/or adipocytes, lowering the temperature of the raw tissue, increasing the internal pressure of the raw tissue, providing vortex and agitation, lowering or raising the osmotic pressure of the suspension or raw tissue, lowering or raising the pH level of the raw tissue, or causing mechanical disruption using blades.

10. The processing system of claim 1, wherein the raw tissue comprises adipose tissue.

11. The processing system of claim 1, wherein the ultrasonic generator is configured to cycle through a range of durations, frequencies and amplitudes according to the size of the cells, cellular structures, cell clusters, collagen fibrils and/or extracellular matrix components.

12. The processing system of claim 1, wherein the valve is configured with a luer lock or port.

\* \* \* \* \*